United States Patent
Bonutti

(10) Patent No.: US 8,739,797 B2
(45) Date of Patent: Jun. 3, 2014

(54) SURGICAL DRAPING SYSTEM

(75) Inventor: Peter M. Bonutti, Effingham, IL (US)

(73) Assignee: Bonutti Skeletal Innovations LLC, Plano, TX (US)

( * ) Notice: Subject to any disclaimer, the term of this patent is extended or adjusted under 35 U.S.C. 154(b) by 0 days.

(21) Appl. No.: 11/538,099

(22) Filed: Oct. 3, 2006

(65) Prior Publication Data

US 2007/0102005 A1 May 10, 2007

Related U.S. Application Data

(60) Division of application No. 10/263,893, filed on Oct. 3, 2002, now Pat. No. 7,114,500, which is a continuation-in-part of application No. 10/191,751, filed on Jul. 8, 2002, now Pat. No. 7,104,996, and a continuation-in-part of application No. 09/976,396, filed on Oct. 11, 2001, now Pat. No. 6,770,078, and a continuation-in-part of application No. 09/941,185, filed on Aug. 28, 2001, now Pat. No. 6,702,821.

(51) Int. Cl.
*A61F 5/37* (2006.01)
*A61F 13/00* (2006.01)
*A61B 19/08* (2006.01)
*A41B 9/00* (2006.01)
*A41D 10/00* (2006.01)

(52) U.S. Cl.
USPC ........... 128/849; 128/846; 128/850; 128/851; 128/852; 128/853; 128/854; 128/855; 128/856; 2/114

(58) Field of Classification Search
USPC ................... 128/849–856, 846; 2/114
See application file for complete search history.

(56) References Cited

U.S. PATENT DOCUMENTS

| | | |
|---|---|---|
| 3,265,059 A | 8/1966 | Matthews |
| 3,669,106 A | 6/1972 | Schrading et al. |
| 3,833,012 A | 9/1974 | McAllister |
| 3,850,172 A | 11/1974 | Cazalis |
| 4,007,741 A | 2/1977 | Waldrop et al. |
| 4,066,089 A | 1/1978 | Rainwater |
| 4,152,792 A | 5/1979 | Glintz |
| 4,471,769 A | 9/1984 | Lockhart |
| 4,556,391 A | 12/1985 | Tardivel et al. |
| 4,559,937 A | 12/1985 | Vinson |
| 4,598,458 A | 7/1986 | McAllester |
| 4,845,779 A * | 7/1989 | Wheeler et al. ............. 2/84 |
| 4,890,628 A | 1/1990 | Jackson |
| 4,944,311 A | 7/1990 | Eldridge, Jr. et al. |
| 4,963,138 A | 10/1990 | Braun, Jr. et al. |
| 4,974,604 A | 12/1990 | Morris |
| 5,002,069 A | 3/1991 | Thompson et al. |

(Continued)

*Primary Examiner* — Patricia Bianco
*Assistant Examiner* — Brandon L Jackson
(74) *Attorney, Agent, or Firm* — Martin & Ferraro, LLP

(57) ABSTRACT

A draping system provides a continuous sterile field between a patient incision area and one or more medical practitioners. The draping system has a quick release system incorporated into the drape that enables a medical practitioner to separate from the continuous sterile field without disrupting the sterile field around the practitioner or the patient. The draping system may include an abbreviated practitioner gown, a drain and an integral patient incision area or a flap for extending the continuous sterile field around to one or more additional operating room tables. A modular drape and gown system extends the sterile field beyond the operating table allowing practitioners to couple to the extended field. A tent provides an enclosed sterile field useful in mobile or other non operating room surgical environments. Integral lighting and information displays facilitate field surgical procedures.

36 Claims, 10 Drawing Sheets

(56) References Cited

U.S. PATENT DOCUMENTS

| | | | | |
|---|---|---|---|---|
| 5,007,912 | A | 4/1991 | Albrektsson et al. | |
| 5,036,866 | A | 8/1991 | Eldrige, Jr. et al. | |
| 5,074,316 | A | 12/1991 | Dowdy | |
| 5,109,873 | A | 5/1992 | Marshall | |
| 5,143,091 | A | 9/1992 | Patnode et al. | |
| 5,197,493 | A | 3/1993 | Grier-Idris | |
| 5,209,243 | A * | 5/1993 | Glassman | 128/849 |
| 5,316,541 | A | 5/1994 | Fischer | |
| 5,342,121 | A | 8/1994 | Koria | |
| 5,419,343 | A | 5/1995 | Taylor | |
| 5,445,165 | A | 8/1995 | Fenwick | |
| 5,494,050 | A | 2/1996 | Reyes | |
| 5,538,012 | A | 7/1996 | Wiedner et al. | |
| 5,609,163 | A | 3/1997 | Beard | |
| 5,611,356 | A | 3/1997 | Rothrum | |
| 5,618,278 | A | 4/1997 | Rothrum | |
| 5,709,221 | A * | 1/1998 | Vancaillie et al. | 128/849 |
| 5,725,426 | A | 3/1998 | Alvarez | |
| 5,765,566 | A | 6/1998 | Rothrum | |
| 5,778,890 | A | 7/1998 | Lofgren et al. | |
| 5,803,086 | A | 9/1998 | Scholz et al. | |
| 5,816,253 | A | 10/1998 | Sosebee | |
| 5,832,919 | A | 11/1998 | Kano et al. | |
| 5,860,420 | A | 1/1999 | Wiedner et al. | |
| 5,975,082 | A | 11/1999 | Dowdy | |
| 5,979,450 | A * | 11/1999 | Baker et al. | 128/849 |
| 5,985,395 | A * | 11/1999 | Comstock et al. | 428/40.1 |
| 5,988,172 | A | 11/1999 | Sosebee | |
| 6,094,801 | A | 8/2000 | Howe | |
| 6,105,579 | A | 8/2000 | Levitt et al. | |
| 6,199,551 | B1 | 3/2001 | Kuslich | |
| 6,286,511 | B1 | 9/2001 | Levitt et al. | |
| 6,321,764 | B1 | 11/2001 | Gauger et al. | |
| 6,346,072 | B1 * | 2/2002 | Cooper | 600/102 |
| 6,405,730 | B2 | 6/2002 | Levitt et al. | |
| 6,461,290 | B1 | 10/2002 | Reichman et al. | |
| 6,582,384 | B1 | 6/2003 | Henry | |
| 6,685,622 | B2 | 2/2004 | O'Connor et al. | |
| 6,945,064 | B2 | 9/2005 | Jebaraj | |
| 7,037,254 | B2 | 5/2006 | O'Connor et al. | |
| 7,114,500 | B2 | 10/2006 | Bonutti | |
| 2006/0021621 | A1 | 2/2006 | Kriek | |
| 2006/0076024 | A1 * | 4/2006 | Duarte | 128/849 |
| 2008/0041399 | A1 | 2/2008 | Kriek | |
| 2008/0047567 | A1 | 2/2008 | Bonutti | |

\* cited by examiner

SURGICAL DRAPING SYSTEM

CROSS REFERENCE TO RELATED APPLICATIONS

This application is a divisional of U.S. patent application Ser. No. 10/263,893 filed Oct. 3, 2002 now U.S. Pat. No. 7,114,500. The aforementioned U.S. patent application Ser. No. 10/263,893 is a continuation-in-part of U.S. patent application Ser. No. 10/191,751 filed Jul. 8, 2002 now U.S. Pat. No. 7,104,996, and a continuation-in-part of U.S. patent application Ser. No. 09/976,396 filed Oct. 11, 2001 now U.S. Pat. No. 6,770,078, and a continuation-in-part of U.S. patent application Ser. No. 09/941,185 filed Aug. 28, 2001 now U.S. Pat. No. 6,702,821.

FIELD OF THE INVENTION

This invention is related to the field of draping systems used to create and maintain sterile fields surrounding operative sites.

BACKGROUND OF THE INVENTION

In a medical operating room environment multiple independent and discontinuous sterile environments are established. A patient is positioned upon an operating room table and a sterile field around the area surrounds the operative site on the patient is created with one or more sterile drapes. Furthermore, medical practitioners are covered with gowns and other garments worn by medical practitioners in the operating room. Medical practitioners include doctors, nurses and other attendants or persons present in the operating room during surgery. The gowns can include various components for covering the head and face of the practitioner as well as the arms, hands and torso of the practitioner. Each gown includes several sterile components and each practitioner wears a separate gown. Furthermore, the operating room includes a wide variety of tables and stands for instruments, implants, trial implants and other surgical implements used during surgery. Each of these tables or stands has its own sterile field. Thus, the operating room has several independent sterile fields including a sterile field around the patient's incision, a sterile field for each practitioner and a sterile field around various operating room tables.

Unfortunately, the area between the sterile fields is not considered sterile. Thus, the area below the operating table and between the operating table and a practitioner is not considered sterile. Furthermore, the area below and between the operating table and an instrument table is not considered sterile. Also, the area below and between the instrument table and a practitioner is not considered sterile. A sterilized instrument is no longer considered sterile if it happens beyond the sterilized fields. Thus, if an instrument such as a scalpel is dropped to the floor during surgery, it drops below the surface of the operating table, is no longer considered sterile and is no longer to be used during surgery. Thus, what is needed is a draping system that allows for a continuous sterile field to be established between at least some of the various independent sterile fields within the operating room.

U.S. Pat. Nos. 4,007,741 and 5,816,253 show draping systems used during delivery of a baby. A drape is tied around the waist or neck of a doctor and attached to the operating table. Unfortunately, the doctor cannot rapidly separate from the draping system in case such a need should arise. Thus, what is needed is a draping system that provides a continuous sterile field between a practitioner and the patient yet allows the practitioner to be rapidly separated should the need arise.

In some surgical procedures, such as artheoscopic knee surgery, it is desirable to allow for an extremity of the patient to extend below the surface of the operating table. Thus, it is desirable to provide for a sterile field that may extend below the surface of the operating table. U.S. Pat. No. 5,494,050 shows a pouch for use during knee surgery that extends below the operating table. However, the pouch does not provide for a continuous sterile field between the practitioner and the operating table. Thus, what is needed is a continuous sterile field extending below the operating table that facilitates surgical procedures where a portion of the patient may be positioned below the operating table.

Several components including drapes and practitioner gowns are used to establish a continuous sterile field between the practitioner and the operating table. What is needed is a draping system that reduces the number of components used to establish the continuous sterile field between the practitioner and the operating table.

Several components including drapes and practitioner gowns are used to establish a continuous sterile field between the practitioner and the patient incision area. What is needed is a draping system that reduces the number of components used to establish the continuous sterile field between the practitioner and the patient incision area.

The surgical operating room has a sterile environment. Making a room sterile for an operation is costly and time consuming. This makes it prohibitive for many doctors to perform surgical procedures in their offices. Furthermore, there are instances where surgical procedures suited for a sterile environment are better performed in the field. Such procedures include organ and tissue harvesting and emergency surgery. The traditional operating room does not lend itself to address these needs. Therefore, what is needed is a sterile surgical environment that is mobile and can be used in surgical procedures performed outside of an operating room.

In the mobile surgical procedure environment, lighting and information display can be problematic. For example, if a late night automobile accident provides an opportunity for an emergency surgical procedure or an organ harvest, a fully equipped operating room is typically unavailable. Such situation requires a sterile and properly equipped environment to complete the surgical procedure at the accident site. A properly equipped environment includes a well lit surgical area as well as information screens conveniently available to facilitate the practitioner in the surgical procedure. Thus, what is needed is a portable or mobile surgical environment that further provides for lighting and display of information in a rapidly deployable manner.

SUMMARY OF THE INVENTION

In accordance with the present invention, a drape is coupled to a patient positioned upon an operating table and providing a continuous sterile field between a practitioner and the operating table. The drape comprises a fastening element for fastening the drape to the practitioner, and a separating element for enabling the practitioner to separate from the continuous sterile field while at least a portion of the drape is still fastened to the practitioner and at least a second portion of the drape is still coupled to the patient.

In accordance with the present invention, an operating room draping system comprises a drape for facilitating a continuous sterile field between a practitioner and an operating table having a patient positioned thereon, and at least a portion of a gown integral to said drape and worn by the practitioner for extending the continuous sterile field to include a sterile field between the patient and the practitioner.

In accordance with the present invention, a surgical drape comprises a first portion of the drape for facilitating a continuous sterile field between a practitioner and an operating table having a patient positioned thereon, and a second portion of the drape for extending the continuous sterile field to a second table.

In accordance with the present invention, a drape for providing at least a portion of a continuous sterile field between a practitioner and a patient surgical area comprises a fastening element for fastening the drape to the practitioner, and an integral incision region for at least partially coupling the drape to the patient surgical area wherein a patient incision is made by simultaneously cutting through said integral incision region and at least a portion of the patient.

In accordance with the present invention, a drape comprises a first portion for facilitating a continuous sterile field between a first practitioner and an operating table having a patient positioned thereon, and a second portion for extending the continuous sterile field to a second practitioner.

In accordance with the present invention, a surgical drape system for providing an extended sterile field comprises a first portion of a drape for providing a sterile field over a patient positioned upon an operating table, an extension portion of the drape for extending the sterile field beyond an edge of the operating table, and a suspension device for suspending the extension portion substantially beyond the edge of the operating table.

In accordance with the present invention, a surgical enclosure having a sterile interior comprises a vent for coupling to an air handler for providing a positive air pressure within the interior, a first portion for providing a sterile field above a patient, and an opening for providing surgical access to the interior.

In accordance with the present invention, a portable surgical enclosure having a sterile surgical interior environment comprises a first portion for providing a first interior sterile field area over a patient positioned upon a first table, and a second portion for providing a second interior sterile field area over a second table.

In accordance with the present invention, a portable surgical enclosure having a sterile surgical interior environment comprises a first portion for providing a first interior sterile field over a patient positioned upon a first table, and a drain for collecting fluids accumulated within the interior.

In accordance with the present invention an illuminating surgical glove comprises a surgical glove having a sterile exterior surface and a light integral to said surgical glove for providing illumination during surgery. The present invention also envisions lights used with other portions of the surgical gown.

In accordance with the present invention, an illuminating surgical drape comprises a surgical drape and a light integral to said surgical drape for providing illumination during surgery.

In accordance with the present invention, an illuminated surgical enclosure comprises a mobile surgical enclosure, and a light integral to said enclosure for providing light to the interior of said enclosure during surgery.

In accordance with the present invention, a surgical drape displaying information comprises a drape, and an information display integrated into said drape for displaying information during surgery.

In accordance with the present invention, a surgical enclosure for displaying information comprises a mobile surgical enclosure, and an information display integrated onto an interior surface of said enclosure for displaying information during surgery.

DETAILED DESCRIPTION OF THE INVENTION

It is important to note, that these embodiments are only examples of the many advantageous uses of the innovative teachings herein. In general, statements made in the specification of the present application do not necessarily limit any of the equivalent and various claimed inventions. Moreover, some statements may apply to some inventive features but not to others. In general, unless otherwise indicated, singular elements may be in the plural and visa versa with no loss of generality.

Figure 1:
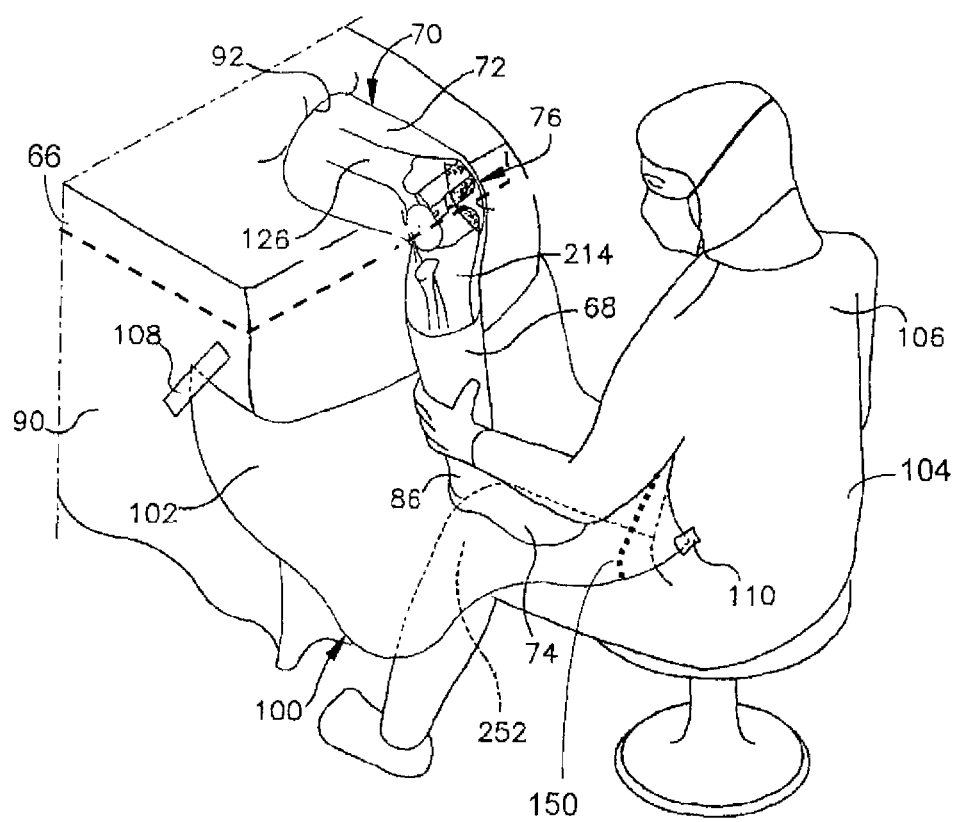
FIG. 1 shows a draping system in accordance with the present invention wherein a continuous sterile field extends below an operating table between a patient and a seated practitioner.
Figure 2:
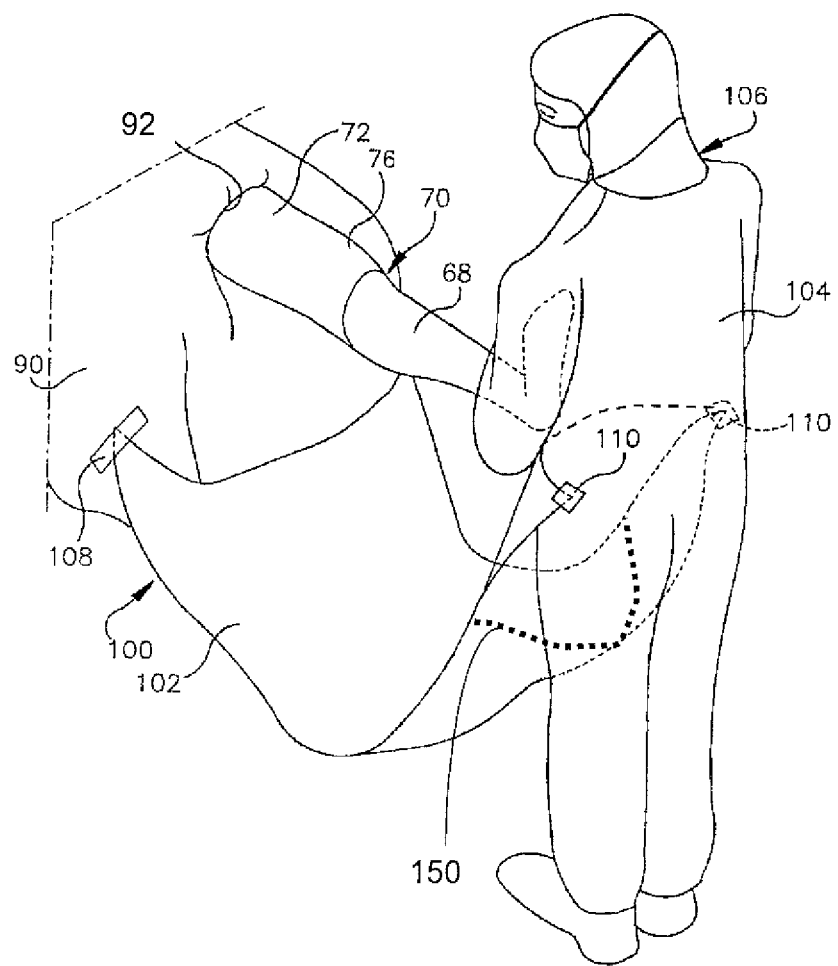
FIG. 2 shows the draping system of FIG. 1 with the practitioner standing.

FIG. 1 shows a draping system in accordance with the present invention wherein a continuous sterile field is established below an operating table during a surgical procedure such as a knee surgery and the practitioner is seated. FIG. 2 shows a draping system in accordance with the present invention wherein a continuous sterile field is established below an operating table during a surgical procedure such as a knee surgery and the practitioner is standing. The practitioner is shown as a surgeon in these figures. However, the practitioner can be any person associated with the surgery or medical procedure, such as other doctors, nurses, medical professionals or observers.

In accordance with FIG. 1 of the invention, the lower portion 68 of a patient's leg 70 is suspended from the upper portion 72 of the leg. This enables the foot 74 and ankle portion 86 of the leg 70 of the patient to be freely moved in any direction or a combination of directions. Thus, the foot 74 and ankle portion 86 of the leg 70 of the patient can be moved anteriorly or upward to decrease the extent of flexion of the knee portion 76 or even to extend or straighten the leg 70.

Alternatively, the foot 74 and ankle portion 86 may be moved posteriorly toward the operating table 66, shown covered by drape 90, to hyperflex the knee portion 76 of the leg of a patient. The foot 74 may be moved sidewardly, that is in either a lateral or medial direction. In addition, the foot 74 may be rotated about the longitudinal central axis of the lower portion 68 of the leg 70.

It is contemplated that the foot 74 and ankle portion 86 may be simultaneously moved in a plurality of the directions previously mentioned. If desired, the upper portion 72 of the leg 70 of the patient may be supported on a separate section of the operating table 66, in a manner similar to the disclosure in U.S. Pat. No. 5,007,912.

After a drape 90 has been positioned over the patient and the operating table 66, in the manner illustrated in FIG. 1, the leg 70 extends out of the drape. The drape 90 may be connected with a leg support and have an opening 92 through which the leg of the patient extends. This enables the leg 70 of a patient to be moved between the extended position illustrated in FIG. 2 and a hyperflexed position in which the foot 74 is disposed posteriorly from the position illustrated in FIG. 1.

When the leg 70 is in a hyperflexed condition, the included angle between the upper and lower portions 72 and 68 of the leg 70 is less than ninety degrees. The leg 70 may be flexed from the extended position of FIG. 2 to a hyperflexed position by manually moving the foot 74 and an ankle portion 86 of the leg 70 relative to the operating table 66 while the upper portion 72 of the leg is held by a leg support (not shown). When the leg 70 is hyperflexed, a portion of the foot 74 may be disposed beneath the operating table 66.

The draping system 100 includes the drape 90 and a drape 102 connected with a gown 104 on a surgeon 106. The illustrated drape 102 is formed separately from the drape 90 and gown 104. However, the drape 102 may be integrally formed as one piece with the drape 90. Alternatively, the drape 102 may be integrally formed as one piece with the gown 104.

In the embodiment illustrated in FIG. 1, the drape 102 is formed separately from the gown 104 and the drape 90. The drape 102 is coupled to the patient through drape 90 by using suitable fastening elements such as clamps 108. The drape 102 is connected with the waist of the surgeon 106 by fastening elements or clamps 110 to the gown 104 and forms a continuous sterile field between the surgeon and the operating table. Rather than utilizing clamps 108 to interconnect the drapes 90 and 102 or clamps 110 to interconnect drape 102 to the surgeon gown 104, the interconnection fastening elements 108 and/or 110 could be by VELCRO, ties, or other known devices including buttons, hooks, snaps, snap drapes, adhesives, and adhesive drapes.

The draping system 100 maintains a continuous sterile field between the leg 70 and the surgeon 106 during movement of the surgeon relative to the patient. Thus, when the surgeon is in a seated position the drapery system 100 provides a sterile field which extends from the surgeon to the space beneath and adjacent to the leg 70. The foot 74 may be supported on the surgeon's knee 252 with drape 102 between. The foot 74 is free to move in any direction relative to the knee portion 76. By raising or lowering his or her knee 252, the surgeon 106 can move the tibia 214 relative to the femur 126 and vary the space between the distal end of the femur and the proximal end of the tibia. When the surgeon stands, as shown in FIG. 2, the drapery system 100 continues to maintain a sterile field between the surgeon and the patient. This enables the surgeon 106 to move the leg 70 of a patient during an operation without contaminating the sterile field. The draping system 100 enables the sterile field to be maintained when the patient's leg is moved between the extended position and a hyperflexed position in which the foot 74 of the patient is disposed beneath the operating table 66.

During movement of the surgeon 106 relative to the patient, for example, between the seated position of FIG. 1 and the standing position of FIG. 2, the drape 102 moves with the surgeon and maintains the continuous sterile field. Thus, when the surgeon 106 moves toward and away from the patient, the end portion of the drape 102 connected with the surgeon also moves toward and away from the patient. As the surgeon moves toward the patient, a portion of the drape 102 between the surgeon 106 and patient is lowered. As the surgeon moves away from the patient, the portion of the drape 102 between the surgeon and patient is raised. The foot 74 connected with the leg 70 of the patient is always above the drape 102 during movement of the surgeon 106. The drape 102 could be such that it extends to the floor during surgery thereby providing a sterile field above and extending down to the floor during surgery.

Fastening elements 110 securely attach drape 102 to the surgeon. If the surgeon needs to change positions, going from one side of the table to another, a quick release system enables the surgeon to separate from drape 102. The quick release system can be implemented with quick release clamps such as hooks or VELCRO. FIGS. 1 and 2 show a quick release system where a tearing system is incorporated into drape 102. The quick release system has a separating element such as a tearing system which is shown as a perforation or serration 150 incorporated within drape 102. The tearing system enables the surgeon to predictably separate from drape 102 by tearing or parting the drape and also allows the surgeon to quickly mobilize if required without unfastening clamps 110. For example, in the event of an emergency the surgeon could rapidly rip drape 102 along the tearing system 150 to be quickly freed from the draping system 102. This separation occurs without disturbing the sterile field of the operating table established by drape 90 or without unfastening clamps 110.

There are other benefits of the quick release system in addition to the time saving feature. For example, serration 150 is placed within the sterile surgical field so that the surgeon can implement the quick release system without compromising sterility. In contrast, if unfastening of clamps 110 were necessary, sterility may be compromised or a non-sterile assistant would have to unfasten clamps 110, which are generally located beyond or at an edge of the sterile field. Thus, serration 150 allows for separation from sterile filed without compromising the sterile field.

Figure 3:
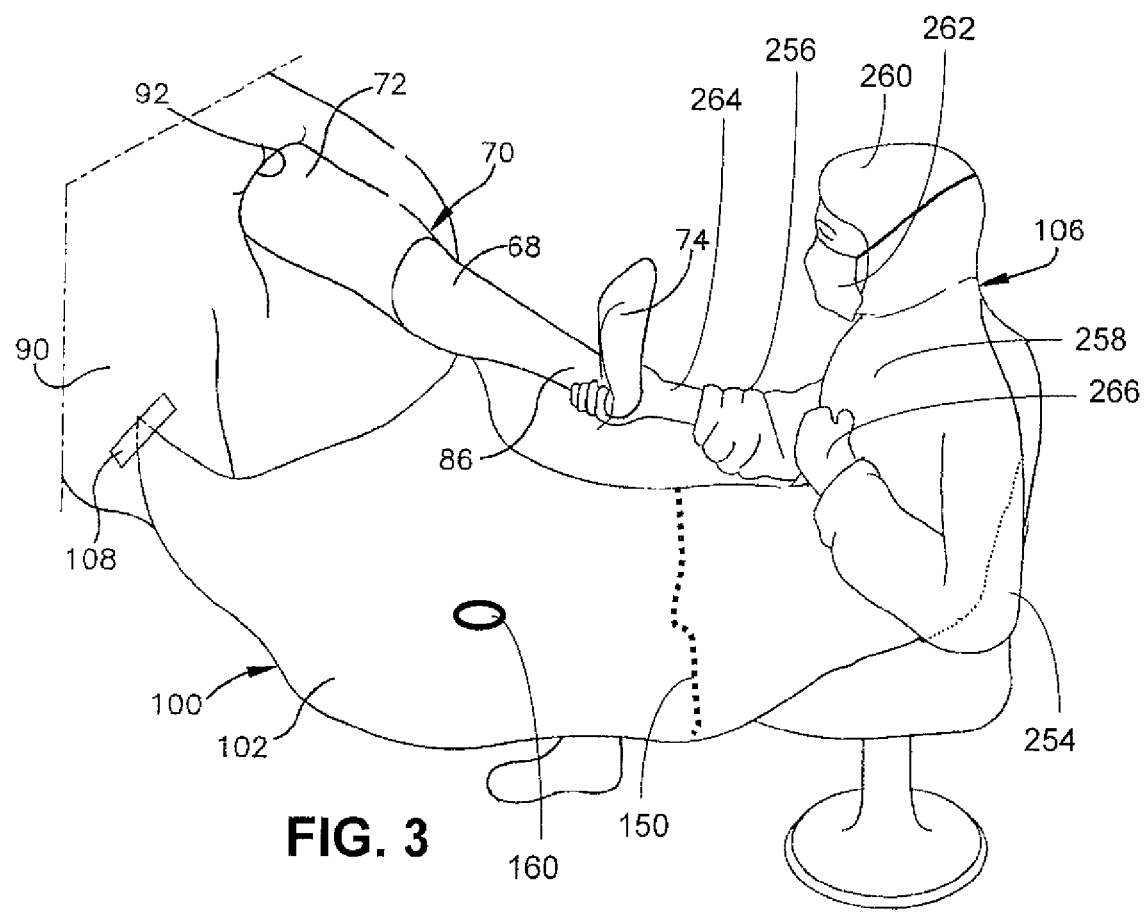
FIG. 3 shows a draping system in accordance with the present invention having a continuous sterile field established between a patient and a practitioner wherein a portion of the surgical gown of the practitioner includes part of the draping system.

FIG. 3 shows a draping system in accordance with the present invention having a continuous sterile field established between a patient positioned upon an operating table and the practitioner wherein at least a portion of the gown of the practitioner includes part of the draping system. The portion of the gown may be incorporated as part of the fastening element for fastening the drape to the surgeon. Drape 102 includes the serrated quick release system 150 as well as a sterile portion including the arms 254 and 256 and torso 258 for covering the corresponding portions of the surgeon 106. Preferably the arms and torso portions of the gown are an integral part of drape 102 and may facilitate at least partially fastening the drape to the practitioner. The head and face have a helmet 260 and mask 262 for facilitating a sterile field between the practitioner and the patient. In the embodiment of FIG. 3, the helmet and mask are separate from the drape. In an alternate embodiment the helmet and mask can be integrated into the drape 102. The surgeon's hands are covered by gloves 264 and 266. In an alternate embodiment the gloves could be integral to the drape 102. The abbreviated surgeon's gown has arms and front torso covering portion as a portion of the drape 102. The surgeon simply puts his or her arms through the abbreviated gown. The gown may be optionally further fastened thereafter using the aforementioned clamps and then gloves applied. Alternatively, the drape may include arm holes in which the practitioner arms are slid through. In this alternative the draping system provides a substantial portion of the continuous sterile field between the patient and the torso of the surgeon.

The abbreviated gown and drape form a continuous sterile field between the surgeon or other practitioner and the operating table. Other practitioners in the operating room may require mobility and have independent surgical gowns. However, the quick release system provides the additional advantage of, upon completing release of the practitioner from the continuous sterile field, maintaining a sterile portion of the gown worn by the practitioner that was included with the draping system. Thus, a practitioner may simply slip into the draping system 102 having a portion of the sterile gown over the practitioner and a continuous sterile field between the surgeon and the patient. However, after the quick release system is used by tearing along the serrated or perforated portion 150, the practitioner now has a mobile sterile gown even though a portion of the gown was an integral component of the continuous sterile field draping system. In this way, the partial gown may be either a component of the continuous sterile field draping system or the mobile sterile field after use of the quick release system.

Drape 102 also has a drain 160. The drape 102 is preferably liquid impervious and flexible. Thus, any liquids or fluids that may collect at the bottom of the drape 102 during surgery may be removed to a remote location through the drain 160. This not only has the advantage of retaining released fluids within the draping system and then draining the fluids away, but since the weight of the continuous draping is at least partially supported by the practitioner, the weight of fluids retained by the continuous draping system are also at least partially supported by the practitioner and transferred through serration or perforation 150. Draining away the fluids via drain 160 not only reduces the weight supported by the practitioner during surgery, but also helps assure that there is a minimal amount of tension on the quick release system 150 assuring it remains attached even though fluids may be released during surgery. The drain may be either gravity fed or have active suction as is known by those familiar with the art. Furthermore the drain may have a filter to allow fluids to drain while retaining tissue within the draping system. The filter may include a mesh or screen. The retained tissue may have advantageous humanitarian applications or may have further application in the surgical or healing process.

Although the drapery system 100 has been illustrated in FIG. 1 to FIG. 3 in association with a patient's leg 70, the drapery system may be used in association with procedures on any desired portion of a patient's body. For example, the drapery system 100 could be used to maintain a sterile field between a surgeon and patient during surgery on a trunk portion of a patient's body. Alternatively, the drapery system 100 could be used to maintain a sterile field during surgery on a head or arm portion of a patient's body.

Figure 4:
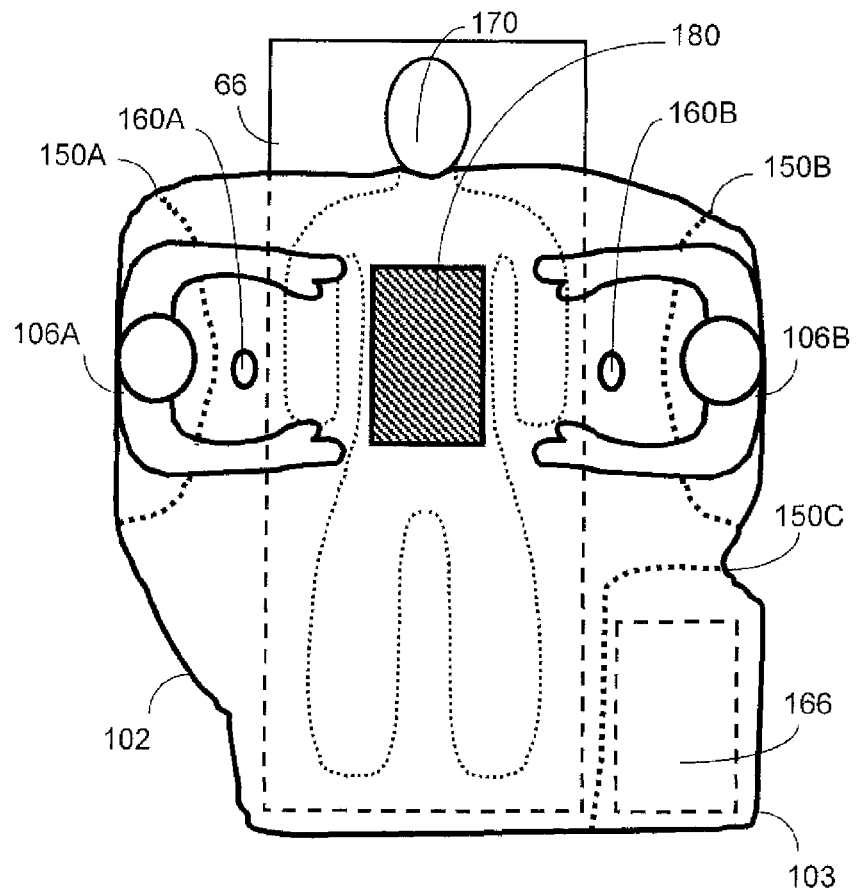
FIG. 4 shows a top view of a draping system in accordance with the present invention having a continuous sterile field established between a patient, multiple practitioners, and multiple surgical tables.
Figure 5:
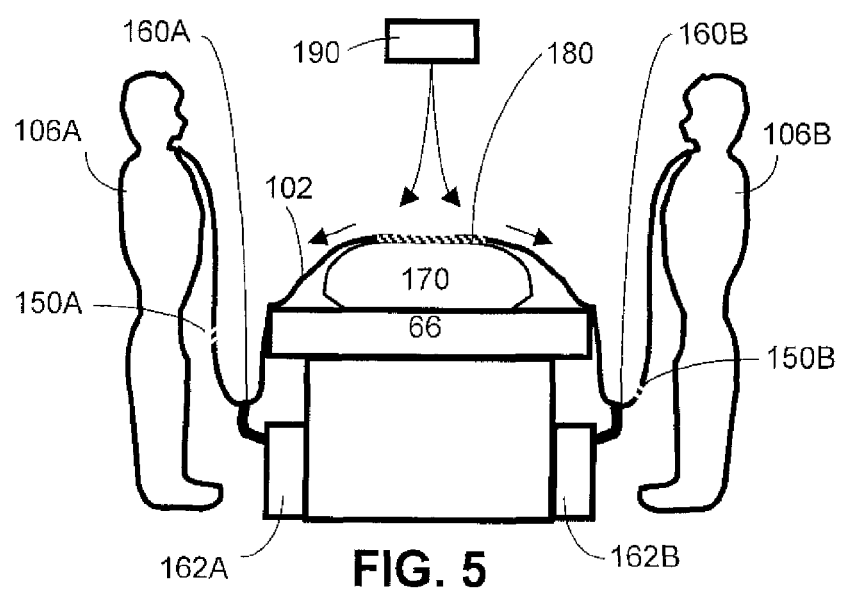
FIG. 5 shows a cross-sectional view of the draping system of FIG. 4.

FIG. 4 shows a top view of a multiple practitioner, multiple table continuous sterilized field draping system in accordance with the present invention. FIG. 5 shows a cross-sectional view of the multiple practitioner, multiple table continuous sterilized field draping system of FIG. 4. Drape 102 is placed upon a patient 170 and attached to two practitioners 106A and 106B who may both be surgeons or a surgeon and an assistant or other combination of practitioners. The drape may be attached by clamps to a practitioner's gown, as shown by FIG. 1 and FIG. 2, or may include at least an abbreviated partial integral gown worn by the practitioner as described herein. The drape may include at least one quick release system 150A and/or 150B and at least one drain 160A and/or 160B as previously discussed. The drape also has a flap or second portion 103 for extending the continuous sterile field to a second table 166. The second table is preferably for surgical instruments used during surgery. The second portion may be clamped to the table and may have pouches, pockets, clips or other retaining means that maintain a position of the surgical instruments such as suction, Bovie, arthroscopic equipment, etc while positioned upon table 166. The second portion of the drape further maintains the sterilization of surgical instruments should they be dropped, brought below the waist of a practitioner or otherwise mishandled while being removed from or returned to the table 166 because the drape prevents the instrument from leaving the sterile field, which but for the second portion 103 of the drape 102 could otherwise drop to the floor.

The drape also has a region 180 having an opening or fenestration through which the surgery is performed. Preferably, region 180 is an integral incision region having a transparent adhesive backed panel wherein a patient incision is made by simultaneously cutting through the transparent panel of the integral incision region. The transparent panel is an integral component of the drape 102 and has an adhesive attached to the transparent panel for adhesively attaching said transparent panel and thus the draping system to the patient surgical area. The adhesive backed transparent panel at least partially couples the drape 102 to the patient and the patient surgical area. Region 180 is a clear, see-through component allowing visualization of the surgical area, and it could have an antimicrobial agent or antibiotic agent such as Betadine impregnated through it.

An air handler 190 provides sterilized air over the area of the incision. Drains 160A and 160B as previously described drain away fluids into containers 162A and 162B. The draping system of FIG. 4 and FIG. 5 provides for a continuous sterile field between the incision area 180, at least one or more practitioners 106A and 106B and several operating tables 66 and 166 while providing for collection of fluids using drains 160A and 160B. The drape 102 could further include a portion or an entire gown including a helmet and mask to be worn by the practitioner. In this embodiment, the practitioner can walk into the draping system.

Figure 6:
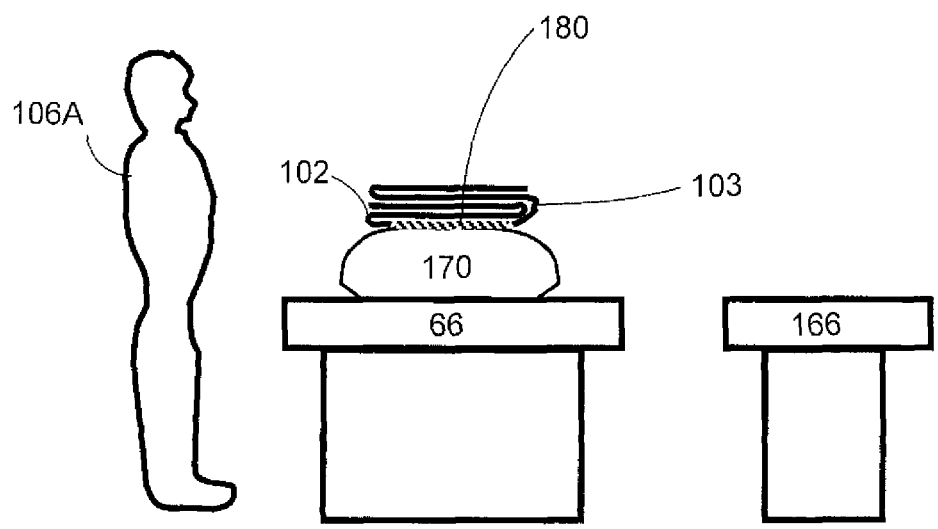
FIG. 6 shows an application where the folded draping system in accordance with the present invention is placed upon the patient prior to surgery.

FIG. 6 shows an application where the folder draping system is placed upon the patient prior to surgery. Patient 170 is placed on the operating table 66, region 180 is adhesively attached to the patient incision area while practitioner 106A and instrument table 166 standby.

Figure 7:
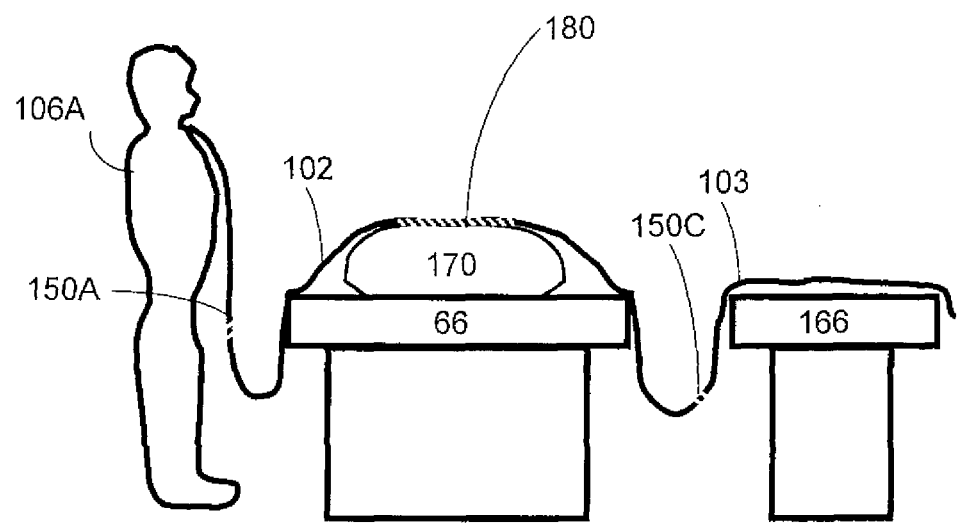
FIG. 7 shows the draping system of FIG. 6 in an unfurled condition providing a continuous sterile field between the patient, practitioner and instrument table.

FIG. 7 shows the draping system of FIG. 6 in an unfurled condition providing a continuous sterile field between the patient 170, practitioner 106A and instrument table 166. Drape 102 is attached to the practitioner to create a continuous sterile field between the patient and the practitioner using any of the attachment means and/or full or partial gowns including those described herein. Furthermore, drape portion 103 is attached to instrument table 166 creating a continuous sterile field there between. Drapes 102 and 103 also have quick release systems 150A and 150C. FIG. 6 and FIG. 7 show that a continuous sterile field can be quickly established by simply unfurling the draping system. The practitioner walks into the gown portion of the draping system thereby providing a readily made continuous sterile field. The system may accommodate multiple practitioners and corresponding continuous sterile fields. Air handler 190 (not shown in FIG. 6 and FIG. 7) provides sterile air during the surgical procedure. Furthermore, should a practitioner need to become mobile, then quick release system 150A and 150B enables separation from the continuous sterile filed while maintaining a sterile field around the patient and the mobile practitioner.

Figure 8:
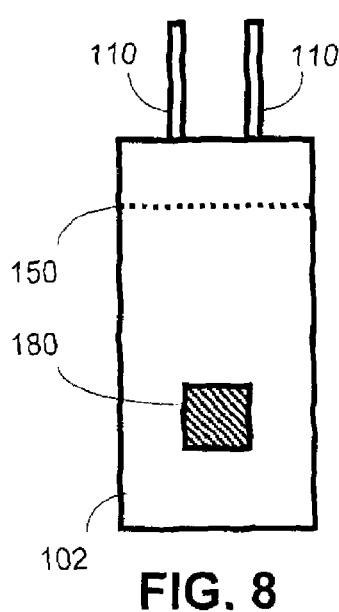
FIG. 8 shows a single practitioner draping system in accordance with the present invention.

FIG. 8 shows a single practitioner draping system in accordance with the present invention. The drape 102 is preferably a flexible impervious sterile material and is attached to the gown of the practitioner using clamps 110. The clamps may be tied around the waist of the surgeon or alternatively may be other clamping means known to those familiar with the art including those previously described herein. Quick release system 150 is included for releasing the practitioner from the draping system without unfastening clamps 110. The drape also has the transparent adhesive back incision region 180 for attachment to the patient incision area. The draping system of FIG. 8 has the advantage of a single integral draping system that provides a continuous sterile field between the practitioner and the incision area and further providing for a quick release of the practitioner without unfastening of clamps while maintaining the sterile field around the incision area.

Figure 9:
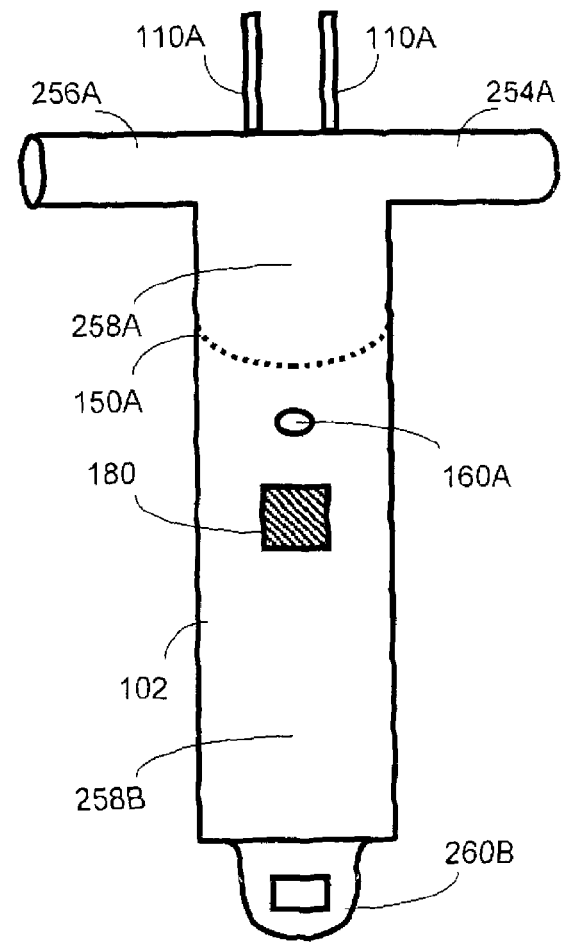
FIG. 9 shows a multiple practitioner draping system in accordance with the present invention.

FIG. 9 shows a multiple practitioner draping system in accordance with the present invention. The drape 102 is preferably a flexible impervious sterile material. The drape includes a quick release system 150A, drain 160A and an incision area 180 as previously described herein. The draping system also includes integral torso 258A and arm portions 254A and 256A of a gown for a first practitioner. The first practitioner slips into the gown portion by sliding arms through sleeves 254A and 256A. The draping system also includes optional clamps 110A for the first practitioner which allow the additional fastening to the practitioner either by a tie around the practitioner's body, adhesive attachment to the a portion of the practitioner's gown or other clamping means known to those familiar with the art.

The draping system of FIG. 9 also includes an integral torso 258B and helmet 260B gown portion for a second practitioner which may at least partially facilitate fastening the drape to the second practitioner. The helmet portion may also include an integral mask or a clear face shield for providing a complete sterile field between the patient or the incision area 180 and the face and head of the practitioner wearing the helmet 260B. In the embodiment shown in FIG. 9, the second practitioner need only slip on the helmet 260B to create the continuous sterile field between the patient and second practitioner. No additional fastening element is shown for coupling the draping system to the second practitioner. In an alternate arms and gloves of a gown may be incorporated into the draping system for the second practitioner. FIG. 9 also shows that the coupling of the draping system between the first and second practitioner need not be identical, rather the draping system can be designed to vary the coupling depending upon the type of surgery or the desires of the practitioners. Furthermore, quick release systems and drains provided for by the draping system may be unique to each practitioner. Further still, the draping system can account for more than two practitioners, and the unified draping system can be designed to cover a portion or substantially all of the patient.

Figure 10:
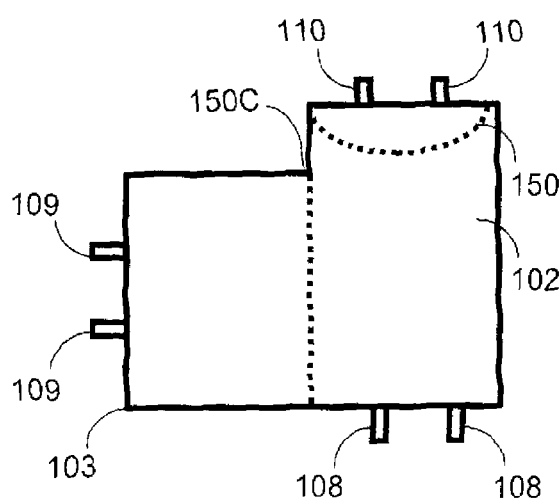
FIG. 10 shows a single practitioner draping system with a second section for covering a second operating room table in accordance with the present invention.

FIG. 10 shows a single practitioner draping system with a second section for covering a second operating room table. The drape 102 is preferably a flexible impervious sterile material. The draping system includes clamps 110 for fastening the draping system to the gown of the practitioner. The draping system includes clamps 108 for coupling to the operating room table upon which the patient is positioned by attaching to another drape or to other operating table components. The draping system includes a quick release system 150 for allowing the practitioner to separate from the continuous sterile field without unfastening clamps 110 or clamps 108. Furthermore, the draping system includes a quick release system 150C for allowing the second table to separate from the continuous sterile field without unfastening clamps 110 or clamps 108. The draping system also includes a second portion 103 for covering a second table in the operating room and for providing a continuous sterile field between the second table and the practitioner and further between the second table and the operating room table upon which the patient is positioned. Preferably the second operating room table is used for placement of surgical instruments. The draping system of FIG. 8 also includes clamps 109 for attaching the draping system to the second operating room table.

FIG. 8, FIG. 9 and FIG. 10 show combinations of various components of the invention. For example, the quick release system may be associated with multiple or single practitioners or need not be incorporated into the draping system. The drain is a similar option. Various components of a practitioner's gown may be incorporated into the draping system providing for a total gown, abbreviated gown or no gown at all for the practitioner. The draping system may be configured to cover multiple operating room tables. The draping system may be configured to cover a portion of the patient and used in combination with other drapes to provide a sterile field around the incision, or the draping system may provide a single unified drape for the operation. The drape may be adapted differently to accommodate different surgical procedures. The drape may include a transparent incision area 180 or an opening for the incision. The draping system facilitates enhanced and simplified sterile environments providing advantages in mobile or field operating rooms.

Figure 11:
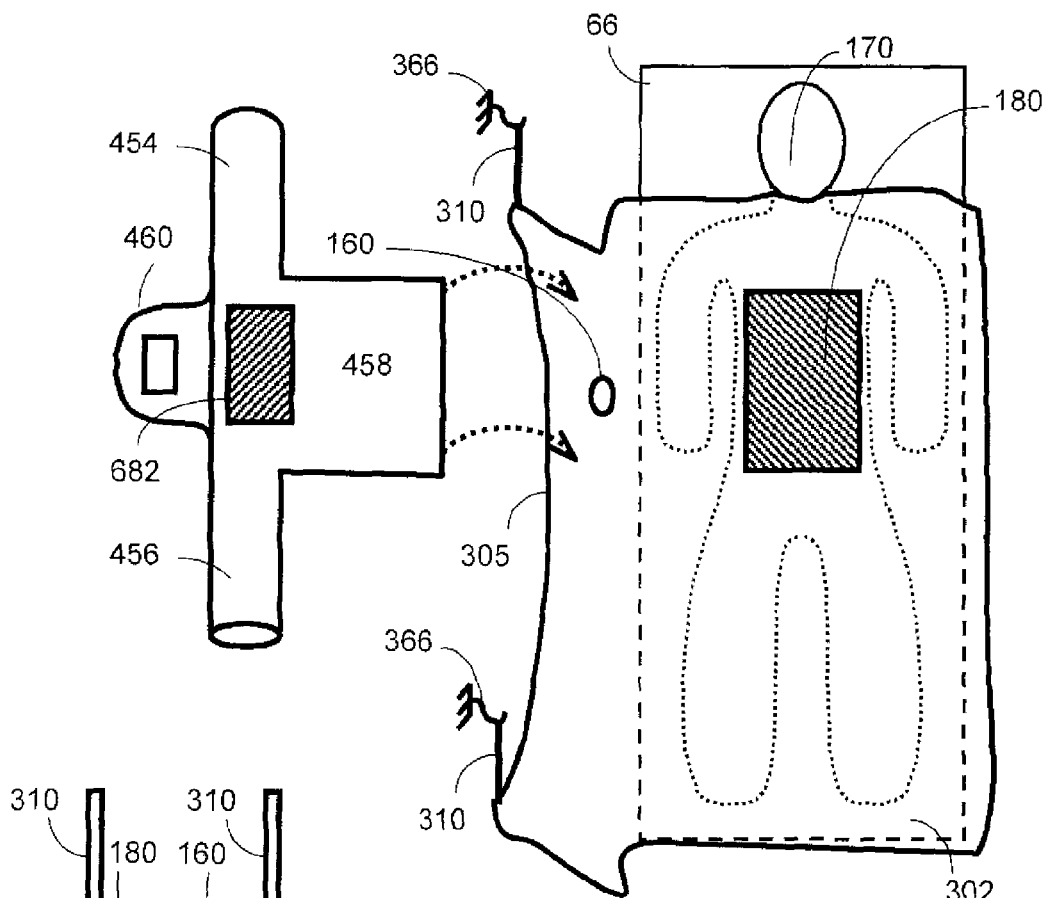
FIG. 11 shows a modular drape and gown system for providing a continuous sterile field between the patient and the practitioner.

FIG. 11 shows a modular drape and gown system for providing a continuous sterile field between the patient and the practitioner. Patient 170 is positioned atop operating table 66 and drape 302 with integral incision area 180 positioned atop the patient. The drape is unfurled and has a drape extension portion 305 extending the sterile field beyond and optionally below the table 66. The extended sterile portion 305 of the drape 302 has an optional drain 160 for collecting fluids as previously described. The extended sterile portion of the drape has fasteners for fastening the drape at points beyond the table so as to suspend the drape extension and extend the sterile field. The embodiment of FIG. 11 shows fastener ties 310 which attach edges of extended portion 305 to hooks 366 to suspend the extended portion 305 at least several inches beyond and partially below the table 66. The hooks form a suspension device for suspending the extension portion substantially beyond the edge of the operating table. In alternate embodiments, the suspension device may be any device adapted to suspend the extended drape 305 beyond the table 66 including a table or a stand. Preferably the hooks 366 are attached to walls of the operating room or alternately may be extended from the table 66 itself. In the embodiment of FIG. 11, the extension of the sterile field is independent of the practitioner being coupled to the patient's drape.

A practitioner's gown has an extended portion 458, a helmet 460 similar to aforementioned helmet 260B, and arms 454 and 456 similar to aforementioned arms 254A and 254B. The sterile field is established by the practitioner coupling the gown extension portion 458 to the extended drape portion 305. The coupling may be a friction coupling or other type of fastener known to those familiar with the art, such as VELCRO, ties, buttons, hooks, clips or adhesives. The alternate embodiments of the practitioner's gown for providing a continuous sterile field between the practitioner and the patient include other configurations described herein.

Figure 12:
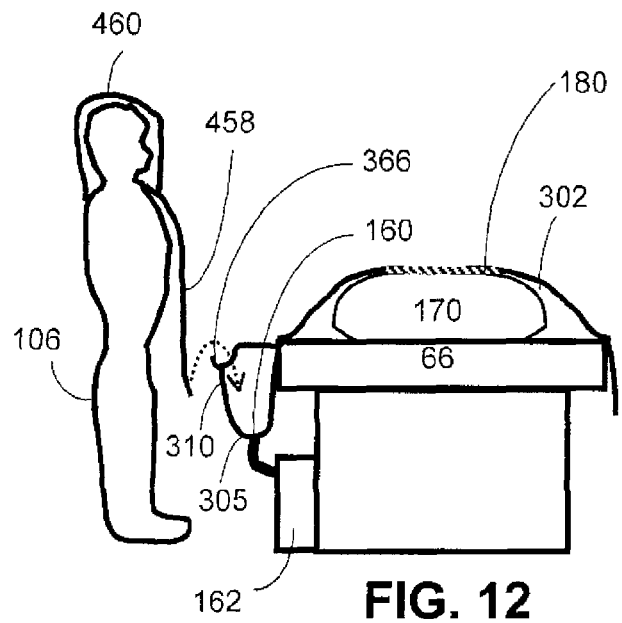
FIG. 12 shows a side view of the modular drape and gown system of FIG. 11.

FIG. 12 shows a side view of the modular drape and gown system of FIG. 11. The drape 302 has an extended portion 305 extending the sterile field beyond and optionally below the surface of table 66. The extended portion is suspended from hooks 366 extending from the table 66. The practitioner 106 is wearing the modular gown having a helmet 460. The continuous sterile field between the practitioner and patient is established when the gown portion 458 is coupled to extended portion 305. The side view shows several advantages of this embodiment. If an instrument or tissue falls into the extended sterile field established by drape portion 305, then it is retained therein without compromising the sterile field or the sterile status of the instrument or tissue. Fluids and their corresponding weight are also readily suspended by hooks 366 rather than practitioners and optionally handled by drain 160 and retainer 162. Furthermore, the suspension system formed by hooks 366 and fasteners 310 extend the sterile field substantially beyond the edge of table 66, at least two inches. Furthermore, the extension of the sterile field is independent of the presence of a practitioner. Thus, the advantages of drape 302 and extended portion 305 may be realized even if conventional prior art surgical gowns are used. Furthermore, practitioners may easily couple their modular gowns to the extended portion 305 to complete the continuous sterile field between the patient and the practitioner. Alternatively, practitioners may use conventional gowns with an extension apron-like gown for coupling to drape extension 305.

This embodiment has the further advantage that practitioner positions and their corresponding continuous sterile field may be established and modified during the surgical procedure without disruption of the extended sterile field established by drape extension 305. For example, a surgeon may initially be positioned at the head of the patient with the gown 458 correspondingly coupled to the extended portion 305 to form the continuous sterile field between the surgeon and the patient. The surgeon's assistant may be positioned to the right of the surgeon with a similar gown 458 that is also coupled to the extended drape 305, thereby providing a second continuous sterile field between the patient and the assistant. If during surgery the surgeon and assistant are to change positions, then they would both decouple from extended drape portion 305, switch positions and re-couple to drape portion 305, the assistant now being at the patient's head and on the left of the surgeon with each advantageously having re-established the continuous sterile field between the patient at their new position.

Figure 13:
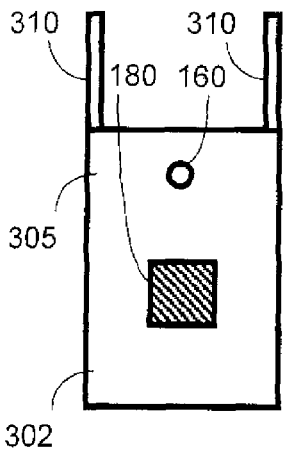
FIG. 13 shows a top view of the drape of FIG. 11 and FIG. 12.

FIG. 13 shows a top view of the drape of FIG. 11 and FIG. 12. The drape 302 has an optional incision area 180 and drain 160. Extended portion 305 and ties 310 extend the sterile field beyond the area of the table. It should be appreciated by those familiar with the art that although the extended sterile field is shown as occurring on a single side of the table, additional extensions may be used to extend the field to multiple sides of the table, affording the aforementioned advantages to the extended sides of the table. It should further be appreciated that the extended sterile field may be extended for a portion of the side of the table or for the entire length of the side of the table. Furthermore, the sterile field may be extended on tables other than the surgical table used by the patient, for example the field may be extended on instrument tables using the teachings provided herein.

Figure 14:
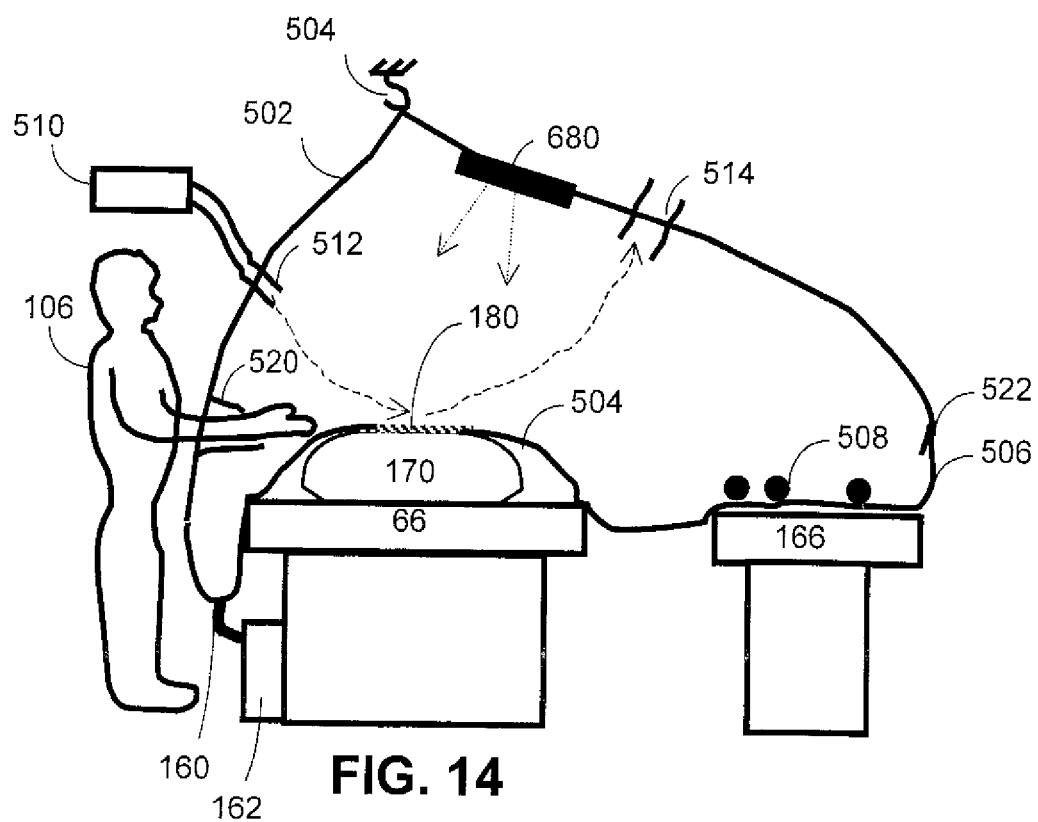
FIG. 14 shows another embodiment of the present invention wherein a continuous sterile field is established within an interior of a surgical enclosure such as a tent.

FIG. 14 shows another embodiment of the present invention wherein a continuous sterile field is established within an interior of a surgical enclosure such as a tent. The tent, 502 is optionally suspended from a hook 504. Alternative means of suspension are anticipated including floor positioned poles that may have inflatable rod and pistons for adjusting the height of the tent. The tent is positioned atop the patient 170 who is positioned upon table 66. The portion 504 of the tent positioned atop the patient may include the previously discussed incision area 180. A second portion of the tent may be positioned atop table 166 which may be used retain surgical instruments 508 positioned thereupon. The interior of the tent is pre-sterilized, providing sterilized areas above the patient 170 and table 166.

A positive pressure in the tent 502 is maintained by air handler 510 which is coupled to vent 512 of tent 502. Air handler 510 also provides sterilized air to the interior of the tent. The vent is optionally adapted to provide a laminar flow of sterilized air over the sterile field above the patient including incision area 180. The air handler may be adapted to modify the air facilitate to the surgical procedure. Modifications of the air include use of ions, thormbin mist or other therapeutic substances known to those familiar with the art. Particularly, such compounds can be used for multiple purposes including reduction of bleeding. Furthermore, the amount of positive pressure in the tent can be regulated. Consequently, patient bleeding may be affected by adjustment of the pressure. Air exit 514 can either exit to the exterior of the tent 502 or return air flow to the air handler 510. The amount of air exiting through air exit 514 and be adjusted to realize a desired pressure within the interior of the tent 502. In a mobile environment, air handler 510 may comprise a tank of compressed and sterilized air sufficient to provide a pressurized interior for a duration of a surgical procedure.

Openings 520 and 522 provide surgical access to the interior of the tent. The arm of a practitioner 106 is shown accessing the interior through opening 520 to perform a surgical procedure. Openings 520 and 522 preferably include first and second overlapping flaps for substantially closing the opening in the absence of surgical access. Furthermore, the flaps separate in response to an arm of a practitioner being inserted through the opening and into the interior of the enclosure. The flaps are situated to minimize the size of any resultant opening to minimize any air escaping from the interior through the opening. An adhesive or other fastening means known to those familiar with the art may be incorporated into the overlapping flaps to minimize an amount of air escaping from the pressurized interior. Although only two openings 520 and 522 are shown, is should be appreciated that a multiplicity of openings may be placed in the tent walls in order to facilitate surgical access at multiple positions and/or multiple practitioners accessing the interior during surgery.

The walls of the tent below the openings may be an opaque surgical draping material while the walls of the tent above the openings may be a transparent material. Thus, the walls of the tent 502 are at least partially transparent.

Previously described optional drain system 160-162 collects fluids during surgery and drains them from the interior of the tent. A filter or mesh may be added to the drain to retain tissues for later use in surgery or for other humanitarian purposes.

The tent 502 and air handler 510 have the advantage of providing for a sterile environment in a location other than a conventional operation room. In order to establish a sterile surgical environment, incision area 180 is adhesively attached to a patient, the tent placed upon the patient, unfurled and pressurized. Thus, a sterile surgical environment can be readily established in a mobile surgical field condition, a doctor's office or other non-conventional area where surgery may be necessary or convenient. The tent can have a portion for covering a second table such as an instrument table for placement of surgical instruments during surgery. The practitioner need not wear a full surgical gown, rather only the portions of the practitioner entering the interior of the tent need have surgical gown components. Furthermore, additional components may be added to the air to facilitate the surgery, or the interior pressure may be correspondingly varied. Upon completion of the surgery, the tent 502 is simply disposed of.

Figure 15:
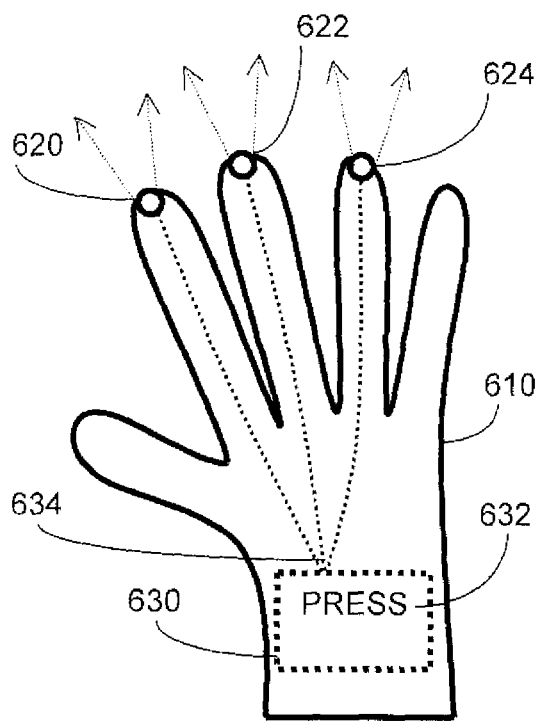
FIG. 15 shows an illuminated glove for use during surgery in accordance with the present invention.

FIG. 15 shows an illuminated glove for use during surgery in accordance with the present invention. The glove 610 has lights 620, 622 and 624 in three of the glove fingers. The lights are situated at the tip of each finger such that light radiates out of the tip. In alternate embodiments light or lights may be placed on other portions of the surgeon or the surgeon's gown such as the helmet, surgical face mask or shield, etc. Additionally, the light or lights may be located at other various locations of the glove including a single finger, such as the index finger, and the direction of the radiation of the light can be changed to different directions. The lights in the glove facilitate the practitioner's view of the procedure at hand. For example, a portable surgical enclosure may be deployed in a field situation where additional lighting may be desirable. In such an application, the lights incorporated within the practitioner's glove provide light for viewing the surgical procedure. Further, if a surgeon were harvesting organs or tissue soon after a late night automobile accident, then the illuminated gloves can provide the surgeon with ready and convenient illumination of the surgical procedure without the requirement of setting up a separate lighting apparatus or the use of an assistant to direct the light to a desired location. Furthermore, the surgical enclosure provides a sterile environment, even though the procedure is being performed in the field.

The glove 610 has an integral power supply 630 and a switch 632 for activating the lights using a wiring connection 634. Preferably the lights are organic light emitting devices (OLEDs). In alternate embodiments, the lights can be any suitable form of illumination including silicon LEDs, electroluminescent devices, miniature incandescent "wheat" bulbs or even chemical lights wherein light is generated in response to a chemical reaction (in which case battery 630, switch 632 and wiring 634 would not be required). The battery 630 is preferably a flexible film battery, other types of power sources are anticipated. Switch 632 is shown incorporated into the battery pack and is switched upon the practitioner pressing on the word "SWITCH" imprinted upon the glove. Other switches known to those familiar with the art are anticipated. Preferably the battery, switch, wiring and bulbs are located on the inside of the surgical glove in order that a sterile exterior surface may be established at the time of manufacture of the glove and maintained during the surgical procedure. Wiring 634 is preferably a "flex" circuit, known to those familiar with the art, and provides for coupling of the battery, lights and switch while facilitating installation inside the glove. Furthermore, incorporating the lights, battery, switch and associated wiring inside the glove provides for the continuous uninterrupted sterile surgical glove surface to which practitioners have become accustom.

Figure 16:
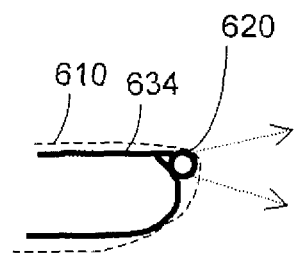
FIG. 16 shows a detail of a light located in the finger tip of a surgical glove worn by a practitioner in accordance with the present invention.

FIG. 16 shows a detail of a light located in the fingertip of a surgical glove worn by a practitioner in accordance with the present invention. The surgical glove 610 comprised of a substantially light transmissive material and light generated by bulb 620 is transmitted through the glove material to provide illumination during surgery. This maintains the sterile outer surface of the glove while providing for illumination during the surgical procedure.

Figure 17:
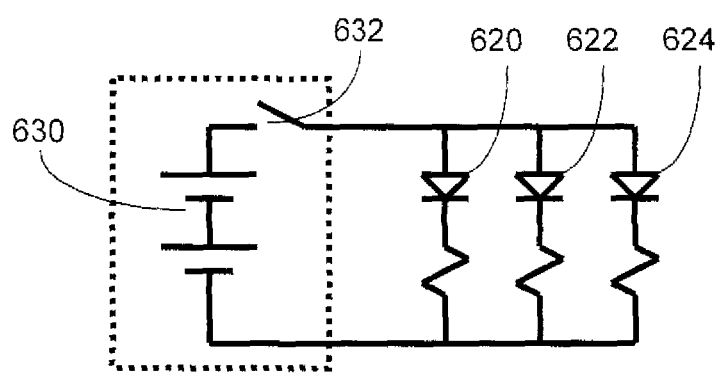
FIG. 17 is a schematic diagram of the illumination circuit for the illuminating surgical glove in accordance with the present invention.

FIG. 17 is a schematic diagram of the illumination circuit for the illuminating surgical glove. A battery 630 is coupled to at least one light 620-624 through a switch 632. Additional bias circuitry may be included. Preferably the battery, switch, lamps and wiring is incorporated on a flex circuit and adhesively attached inside of the surgical glove. Alternate methods of integrating the lights into the surgical glove are also anticipated. The illuminated surgical glove has the advantage in that the glove and lighting system form a single integral unit put on by the practitioner prior to surgery. Also, the unit is disposable after surgery, thereby avoiding any issues with sterilizing the illumination unit between surgical procedures. Components of the disposed of unit may be optionally salvaged for re-use.

Figure 18:
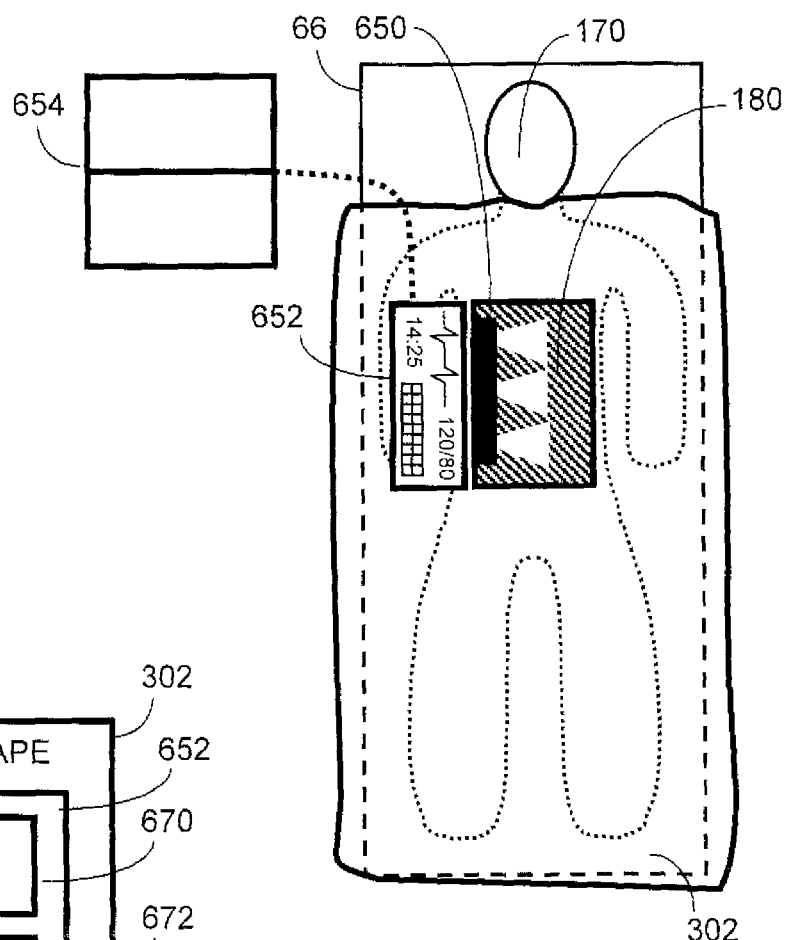
FIG. 18 shows a surgical drape having an integral illuminated fenestration and an integral information display in accordance with the present invention.

FIG. 18 shows a surgical drape having an integral illuminated fenestration and an integral information display. The illuminated fenestration provides lighting for the surgical procedure and may be an integral component of the drape. Patient 170 is positioned upon an operating table 66 and is covered with drape 302. Schematically the lighting is similar to the schematic of FIG. 17. Lighting can be included in a lighting apparatus 650 which may be a bar or ring surrounding the fenestration 180 which is an integral incision region having a transparent adhesive backed panel. A patient incision is made by simultaneously cutting through the transparent panel of the integral incision region and a corresponding portion of the patient while being illuminated by lighting apparatus 650. Region 180 is a clear, see-through component allowing visualization of the surgical area, and it could have an antimicrobial agent or antibiotic agent such as Betadine impregnated through it. The lighting apparatus 650 and the transparent panel are preferably an integral component of the drape 302. In an alternative embodiment, the lighting apparatus 650 may be incorporated into the transparent panel 180, separate from the drape. Or, the lighting apparatus may be incorporated into the drape without the transparent panel. These embodiments provide convenient illumination of the surgical area in that the illumination is provided upon installation of the drape or fenestration having the integral lighting apparatus, thereby enhancing lighting of surgical procedures or facilitating surgical procedures in poorly lit environments such as field surgical procedures.

FIG. 18 also shows a surgical display integrated into the drape in accordance with the present invention. The surgical display 652 is coupled to equipment 654 and provides the practitioner with information including information related to the surgical procedure. The display has the advantage of being incorporated or integrated into the drape thereby allowing for convenient viewing by the practitioner during the surgical procedure. The surgical display 652 is preferably a flexible color display panel integral to the drape and incorporated into the drape prior to surgery. The surgical display panel can be comprised of an organic light emitting device (also referred to as organic light emitting diodes and organic light emitting display OLED) or other technologies that facilitate integration of a display into a surgical drape. The display panel provides a sterile surface for the surgical procedure and complements the sterile surface of the drape.

Figure 19:
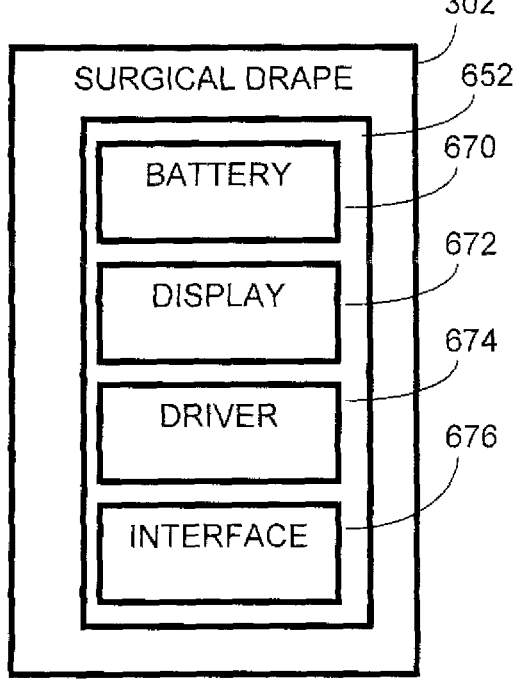
FIG. 19 shows a block diagram of the surgical display in accordance with the present invention.

FIG. 19 shows a block diagram of the surgical display in accordance with the present invention. A battery 670 powers the display 672, a display driver 674 and an interface 676 for communicating with equipment 654. Preferably the communication is wireless using a local area network such as the WiFi network defined by the 802.11b standard. Other wireless or wired interfaces are anticipated. If a wired interface is used, then battery 670 is optional because power for the display can be provided by equipment 654. The wireless interface allows the convenient application of the surgical drape with the integral display in that the display is installed and ready upon installation of the drape. This is highly advantageous in field surgical applications where locating equipment 654 may be problematical. Furthermore, information displayed on the display may be remotely generated, at a hospital for example, and communicated to the display in the field. The display information may include information relevant to the patient or instructions or advice from another remotely located practitioner.

It should be appreciated that alternate lighting panels are also anticipated. A lighting panel can be incorporated into a drape or a wall of a surgical enclosure. A lighting panel incorporated into the wall of a surgical enclosure is shown as panel 680 of FIG. 14. This lighting panel provides illumination within the surgical enclosure. A lighting panel can also be incorporated into a practitioner's gown to provide lighting in the area of the practitioner. Such a lighting panel is shown in FIG. 11 as panel 682. These lighting panels can be self-powered as previously discussed.

The aforementioned lighting panels, lighting apparatus and surgical display have the advantage of a single integral unit that is assembled prior to surgery providing for quicker and simpler deployment of the surgical environment. Also, the lighting panels, lighting apparatus and surgical display can be disposable after surgery along with the drape or surgical tent enclosure, thereby avoiding any issues with sterilizing between surgical procedures. Alternatively, components of the disposed of lighting panels, lighting apparatus and surgical display may be salvaged for subsequent re-use.

It should be appreciated that the lighting apparatus 650 and/or display 652 may be incorporated into a surgical enclosure. Such a surgical enclosure is advantageous in field applications in that not only is a sterile environment readily established by the enclosure, but the enclosure further provides both lighting and an information display for use by the practitioner during the surgical procedure. Since the lighting and display are integral to the enclosure, the time and effort required to set up the procedure is significantly reduced.

CONCLUSION

The draping system according to the present invention can use disposable drapes, preferably (some portions may be resterilizable and, accordingly reusable) with known current systems from commercial sources, including using technology of disposable independent drapes—¾ sheet, disposable adherent drapes—U-drapes, disposable adhesive drapes, Betadine drapes, VELCRO attached drapes, snap—plastic snap drapes, adhesive drapes, single piece drapes, multi drapes, two layer drapes, clear plastic drapes, independent or attached to drapes, one piece drapes with stretchable segment for extremities—arthroscopic drapes, shoulder drapes which incorporate U-drapes, square drapes, etc. multiple companies including using technology of disposable independent drapes—¾ sheet, disposable adherent drapes—U-drapes, disposable adhesive drapes—sticks to skin, Betadine drapes, Velcro attached drapes, snap—plastic snap drapes, adhesive drapes, single piece drapes, multi drapes, two layer drapes, clear plastic drapes, independent or attached to drapes, one piece drapes with stretchable segment for extremities—arthroscopic drapes, shoulder drapes which incorporate U-drapes, square drapes, etc.

The draping system allows a sterile field directly or modularly attached to the surgeon and/or assistant.

The drape can be adhesive drape. Part of the system could have a Betadine adhesive or a clear plastic adhesive which covers the skin where one would operate. This can be clear, see through the surgical area, or it can have antibiotics or Betadine impregnated through it. This can be a two layer drape with a larger drape below which sticks to the patient or is loosely attached to the patient and a narrower surgical field drape above for two layer draping. It can have attachments for surgical instruments such as suction, Bovie, arthroscopic equipment, etc. The drape can have a large pouch to collect all fluid, body parts, blood etc. so it does not drain all over the floor and could collect this in an easily disposable fashion.

The drape can be attached to the surgeon and assistant with adhesive, VELCRO, snap, plastic snap, clip which is disposable or sterilizable. This can be a separate sheet which can attach to the surgeon and patient or it can be a quick release with some serrated edges to allow the surgeon to tear away. The drape could be fairly flexible and could have flexed sections or may have a large redundant area which would go down to the surgeon's knees or to the floor to maintain the sterile field (by typical sterile technique anything below a surgeon's waist level is considered un-sterile or below the hospital bed). However, with this system, if the drape happens to drop down to the floor it creates a contiguous sterile field and therefore, surgeon could retrieve dropped objects from the floor if it is contained within the drape.

This can be a one piece system with flaps to the surgeon and assistant or could be a multi-piece system. It allows movement, twisting, sitting to standing. If the surgeon needs to change positions, going from one side of the table to another, there can be a quick release system. There also can be a tearing system in emergencies, possibly serrated system to allow the surgeon or assistant to leave if necessary.

The drapes can also be used to create a mobile field. Specifically, the drapes can be made to have a surgeon's helmet attached to it and part of a surgeon's gown attached to it so that the surgeon would literally walk into the drape, his hands and his face would go into the drape to create a mobile surgical field attached to the patient to create even more of a sterile field. It can have laminar flow system connected to it to create sterile air coming in and then a suction coming out so it could have unidirectional air flow to further sterilize the field.

The mobile field can have a tent, a cover over the top of this to create a mobile surgical field so that this could be done in emergency setting such as a military field or outdoors. Attaching in flowing air and out flowing air, maintaining super sterile air, this can also be used for tissue harvesting, bone harvesting, organ harvesting under an emergency situation. It can have the surgeon's gown, face mask, sterilizable hood all attached as part of it. It can be unrolled as one sterile pack adhering to the patient and rolling outward and the surgeon simply walks into the drape as does the assistant. When the procedure is complete, simply roll up the drape and throw it away maintaining all contaminated body parts, tissue issues.

The drape can have a sterile flap where instruments can be passed through, can have a simple opening where the assistant or scrub nurse can deliver instruments required through this field or the drape could be a flat open sheet where the assistant can bring the instruments on top of the sterile surgical field. There can also be a separate attachment for the circulating nurse.

There can also be a separate flap which would cover all the surgical tables where the instrument would be applied to the instrument table—Mayo stand, rotating table, moving table, would have a drape which would unfurl and cover them and also make them part of the surgical field so the nurse simply opens the pack up and covers her surgical tables, Mayo stands, etc. and lays the instruments over this after then entire case is unfurled.

This can combine all known existing draping system or add systems such as a quick release drape, extended drapes, modular drapes, procedure specific drapes, all in one drape, instrument attached drapes. Many of the methods can be extremely valuable as creating this mobile field where the existing concepts of what is a "sterile field" would be modified where the surgeon can sit down, stand up, move around. The sterile field can extend below the waist.

The drape can also include an abbreviated surgeon's gown (simply with the arms and front portion of the gown), that would be a portion of the drapes so one would not worry about the draping down to the floor, it would simply have arm holes so that the surgeon can put his arms through there and the nurse would put gloves on him once they are sterilized. One person may need an independently moveable surgical gown, but otherwise the drape itself may have surgical hand holds through that to allow surgeon to stick his arms through it and the hands are simply draped with gloves, but the hand holes and front part of the gown are actually part of the drape and is included in the packs. It is a modified gown with hand holes in front of the gown that are actually part of the drape which then attaches to the patient all as one unit. This appears as a marriage of half of surgeons gown with half of a free drape bonding to the patient's.

Organic Light Emitting Devices or OLED's can be used in the surgical draping concepts. For example, this disposable light emitting device can be sterilizable and placed on a practitioner's index finger or a practitioner's disposable gloves or gowns. This could permit light while a surgeon is working in the field, not having a bulky overhead light. This would then accommodate for the tent-like disposable sterilizable operating room enclosure system. These OLED's also would have the ability for a flexible visual screen where practitioners could see either through a small strip in their glasses or their gowns or the draping system. In the clear plastic hoods there could be a strip of disposable light emitting devices where we could see a computer such as a heads up display or see monitors rather than having a formal TV screen required in the room. The display can be part of the actual "space suit" we describe, the sterile hood enclosure system with its own breathing apparatus, or in a separate portion of the drape. This can be multi use if it is separate and adjacent to the drapes, but as it is flexible it can be mounted in the usual locations and more accessible places. The display can be easily moved up close to the surgeon's field so such a large bulky television screen is not used, or on a single use basis it could be built into the surgeons "bubble" of the sterile field surrounding the head so there may be a strip or a portion in glasses or disposable bubble which can be used on each case. Light can also be transmitted from this area and can be both for optics and for surgical light source.

This technology is suited for the surgical environment especially because of its disposable, sterilizable and/or single use application. The light emitting devices can be built into our disposable gloves as either a light source or as a vision screen.

In view of the above description, there are many different features to the invention. It is contemplated that these features may be used either alone or in combination. It should be understood by those familiar with the art that numerous modifications and equivalent features may be substituted without departing from the spirit and scope of the invention. The scope of the invention is not to be restricted, therefore, to the specific embodiments described, and that equivalent applications, modifications, and embodiments within the scope of the invention are contemplated.

I claim:

1. An operating room draping system for an operating table having a patient positionable thereon, comprising:
    a drape having a first portion sized to cover at least a portion of the patient, a second portion integrally formed as a unitary one piece with said first portion, extendable in a direction away from the patient, and a third portion integrally formed as a unitary one piece with said second portion and configured to be worn by a practitioner, a detaching system located between the second portion and the first portion or the third portion, the detaching system enabling separation of the second portion from the first portion or the third portion, the practitioner thereby being separable from said drape without a requirement to remove said third portion from the practitioner, and without disturbing a sterile field associated with the operating table.

2. The draping system according to claim 1, wherein the drape includes an integral incision region for at least partially coupling said drape to a patient surgical area wherein a patient incision is made by simultaneously cutting through said integral incision region and at least a portion of the patient.

3. The draping system according to claim 2, wherein at least a portion of said integral incision region contains an antibiotic or antimicrobial agent.

4. The draping system according to claim 2, wherein said integral incision region comprises:
    a transparent panel for placement of said integral incision region upon the patient surgical area; and
    an adhesive attached to said transparent panel for adhesively attaching said transparent panel to the patient surgical area wherein the patient incision is made by simultaneously cutting through said transparent panel and at least a portion of the patient.

5. The draping system according to claim 2, wherein said integral incision region is disposed inferiorly when the draping system is packed in a folded condition.

6. The draping system according to claim 1, further comprising a drain for collecting fluids in the second portion.

7. The draping system according to claim 6, wherein said drain is gravity fed or has active suction.

8. The draping system according to claim 6, wherein said drain includes a filter for draining fluids while retaining tissue within the drape.

9. The drape according to claim 1, further including a light integral to said drape for providing illumination during surgery.

10. The surgical drape according to claim 9 further comprising a fenestration through which surgery is performed and wherein said light illuminates said fenestration.

11. The surgical drape according to claim 9 wherein said light is comprised within a flexible illuminating panel disposed upon said surgical drape.

12. The surgical drape according to claim 11 wherein said flexible illuminating panel includes an organic light emitting device and has a sterile surface.

13. The draping system according to claim 1, wherein the drape further comprises a second integral extension portion extending to a second table, the second integral extension portion configured for extending the continuous sterile field between the practitioner and the operating table to the second table.

14. The draping system according to claim 13, wherein the drape further comprises a third integral extension portion extending to a second practitioner, the third integral extension portion configured for extending the continuous sterile field between the practitioner and the operating table to the second practitioner.

15. The draping system according to claim 1, wherein said first portion and said third portion are separable from said second portion by a detaching system.

16. The draping system of claim 15, wherein the first portion and the second portion integrally formed as a unitary one piece.

17. The draping system according to claim 1, wherein said second portion provides a substantial portion of the sterile field between the patient and the practitioner's torso.

18. The draping system according to claim 1, wherein said second portion provides a substantial portion of the sterile field between the patient and the practitioner's head.

19. The draping system according to claim 1, wherein said second portion provides a substantial portion of the sterile field between the patient and the practitioner's arm.

20. The draping system according to claim 1, wherein said second portion provides a substantial portion of the sterile field between the patient and the practitioner's hand.

21. The draping system according to claim 1, wherein said second portion provides a substantial portion of the sterile field between the patient and the practitioner's face.

22. The draping system according to claim 1, wherein said detaching system comprises a perforation or serration within said drape allowing the practitioner to separate said first portion from said second portion, or said third portion from said second portion, along said perforation.

23. The draping system according to claim 1, further comprising:
a suspension device for suspending the drape substantially beyond an edge of the operating table independently of the patient and the practitioner when the draping system is unfurled.

24. The draping system according to claim 1, wherein said at least a portion of the gown is unfurled onto the practitioner without lifting said drape from the patient.

25. The draping system according to claim 1, wherein the draping system is configured in a folded condition for packaging in one piece.

26. The draping system according to claim 1, wherein said portion of a gown includes a portion configured for wearing upon at least the practitioner's torso, head, arm, face, or hand.

27. A method for establishing a continuous sterile field between independent sterile fields in an operating room, the method comprising:
placing the draping system of claim 1 in a first sterile field in a folded condition;
unfurling the draping system to cover at least a portion of a patient in the first sterile field with said first portion;
extending the second portion of the draping system to a second sterile field; and
covering at least portion of a practitioner in a second sterile field with said third portion, whereby the first sterile field is connected to the second sterile field establishing a continuous sterile field.

28. The method according to claim 27, wherein the first sterile field is an operating table with the patient positioned thereon and the second sterile field is the practitioner and an area occupied by the practitioner.

29. A surgical drape system for use by a surgical practitioner in a surgical theatre, the drape comprising:
a first drape configured and dimensioned for covering at least a portion of an operating table having a patient positionable thereon, the first drape establishing a sterile field at and above a height of the operating table; and
a second drape removably attachable to the first drape for extending the sterile field beyond an edge of the operating table, the second drape having a first position in which the extended sterile field includes a descending surface extendable below the height of the operating table substantially down to the floor during surgery and an ascending surface extendable from the bottom portion of the descending surface to about the height of the operating table, the second drape having a second position in which the extended sterile field includes a surface extending above the height of the operating table, the second drape connectable to an object in the surgical theatre to be thereby configured to be moveable from the first position to the second position the ascending surface suspendable at a position substantially beyond an edge of the operating table.

30. The surgical drape system of claim 29 further comprising a fastening element for removably attaching the second drape to the first drape.

31. The surgical drape system of claim 30 wherein the fastening element includes at least one of a clamp, a hook and loop fastener, a tie, a button, a hook, a snap, and adhesive.

32. The surgical drape system of claim 31 wherein the fastening element includes an adhesive.

33. The surgical drape system of claim 30 wherein the second drape includes a pouch.

34. The surgical drape system of claim 33 wherein the pouch is present with the second drape in the second position.

35. The surgical drape system of claim 30 wherein the second drape maintains the sterile field as a surgical implement is moved above and below the operating table.

36. The draping system of claim 29, wherein the object in the surgical theatre is moveable from a first position to a second position, to thereby move the second drape from the first position into the second position.

\* \* \* \* \*